US00PP35459P2

(12) United States Plant Patent
von Tubeuf

(10) Patent No.: US PP35,459 P2
(45) Date of Patent: Nov. 7, 2023

(54) POINSETTIA PLANT NAMED 'NPCW22405'

(50) Latin Name: *Euphorbia pulcherrima*
Varietal Denomination: NPCW22405

(71) Applicant: KLEMM + SOHN GMBH & CO. KG, Stuttgart (DE)

(72) Inventor: Guido von Tubeuf, Stuttgart (DE)

(73) Assignee: KLEMM+ SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/085,878

(22) Filed: Dec. 21, 2022

(51) Int. Cl.
*A01H 5/12* (2018.01)
*A01H 6/14* (2018.01)

(52) U.S. Cl.
USPC ..... Plt./304

(58) Field of Classification Search
USPC ..... Plt./304
CPC ... A01H 5/02; A01H 5/12; A01H 5/00; A01H 6/38; A01H 6/385
See application file for complete search history.

(56) References Cited

PUBLICATIONS

Adam Poinsettias—PennState Extension Poinsettias—What's New with this Old Plant, retrieved on Mar. 7, 2023 at https://extension.psu.edu/poinsettias-whats-new-with-this-old-plant, 2 pp. (Year: 2021).*
Selecta One Poinsettia Early Elegance Series, retrieved on Mar. 7, 2023 at https://www.selectanorthamerica.com/poinsettias/SeriesInfo/?phid=050009520005863, 4 pp. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new *Poinsettia* plant particularly distinguished by having a medium vigor and white bract color, is disclosed.

1 Drawing Sheet

Genus and species: *Euphorbia pulcherrima.*
Variety denomination: 'NPCW22405'.

BACKGROUND OF THE NEW PLANT

The present invention comprises a new and distinct variety of *Poinsettia*, botanically known as *Euphorbia pulcherrima* and hereinafter referred to by the variety name 'NPCW22405'. 'NPCW22405' was derived from a population of irradiated cuttings of the *Poinsettia* variety 'NPCW22279' in November 2017 in Stuttgart, Germany. In May 2018, a branch mutation found from the irradiated cuttings of *Poinsettia* variety 'NPCW22279' (U.S. application Ser. No. 18/084,823, filed Dec. 20, 2022) and subsequently named 'NPCW22405'. In May 2018, 'NPCW22405' was first vegetatively propagated by apical cuttings. 'NPCW22405' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. White bracts; and
2. Medium vigor.

DESCRIPTION OF THE PHOTOGRAPH

This new *Poinsettia* plant is illustrated by the accompanying photograph which shows an overall view of the plant. The photograph is of a plant approximately thirteen-weeksold, grown indoors in Borgo Bainsizza, Italy in November 2022. The colors shown are as true as can be reasonably obtained by conventional photographic procedures.

DESCRIPTION OF THE NEW VARIETY

The following detailed descriptions set forth the distinctive characteristics of 'NPCW22405'. The data which define these characteristics were collected from asexual reproductions carried out in Borgo Bainsizza, Italy. Data was collected on fourteen week old plants grown indoors in Borgo Bainsizza, Italy under greenhouse conditions in November of 2022. Color references are to The R.H.S. Colour Chart of The Royal Horticultural Society of London (R.H.S.), 5$^{th}$ edition (2007).

Classification:
*Family.*—Euphorbiaceae.
*Species.—Euphorbia pulcherrima.*
*Common name.—Poinsettia.*
*Variety.*—'NPCW22405'.

Parentage: Branch mutation from variety 'NPCW22279' (U.S. application Ser. No. 18/084,823, filed Dec. 20, 2022).

Plant:
*Form.*—Triangular.
*Growth habit.*—Upright.
*Height.*—35.0 cm.
*Width.*—55.0 cm.
*Average number of inflorescences per plant.*—5.
*Keeping quality.*—Very good.
*Time to produce a cutting.*—5 to 6 weeks.
*Flowering response time.*—Approximately 50 days.

Propagation:
*Type cuttings*.—Apical cuttings.
*Time to produce a rooted cutting*.—5 to 6 weeks.
*Rooting habit and root color*.—Freely branching and RHS NN155C (White).

Lateral branches:
*Color*.—RHS 143C.
*Stem anthocyanin*.—Not present.
*Length*.—29.0 cm.
*Internode length*.—2.0 cm to 3.5 cm.
*Diameter*.—0.4 cm to 0.6 cm.
*Branching habit*.—Freely branching.
*Number of lateral branches per plant*.—5.
*Texture*.—Smooth.
*Strength*.—Strong.

Leaves:
*Quantity*.—7 to 9 per lateral branch.
*Arrangement*.—Alternate.
*Number of lobes on the leaf blade*.—None (almost entire).
*Lobation depth*.—Almost entire.
*Depth of the deepest sinus of the leaf blade*.—0.2 cm.
*Shape*.—Obtuse.
*Apex*.—Acuminate.
*Base*.—Rounded.
*Margin*.—Almost entire.
*Length*.—12.0 cm to 14.0 cm.
*Width*.—6.0 cm to 9.0 cm.
*Texture*.—Upper surface: Smooth. Lower surface: Slightly pubescent.
*Vein color*.—Upper surface: Transparent, underlying colour of the leaf becomes visible. Lower surface: RHS 145C.
*Variegation*.—Absent.
*Venation pattern*.—Reticulate.
*Color*.—Mature foliage: Upper surface: Closest to RHS 139A. Lower surface: RHS N138B. Immature foliage: Upper surface: RHS N137D. Lower surface: RHS 137C.
*Transitional leaves*.—Present, number is few with weak lobation.
*Leaf petiole*.—Length: 3.0 cm to 6.0 cm. Diameter: 0.2 cm to 0.3 cm. Color: Upper and lower surfaces: RHS 142B. Lower surface anthocyanin coloration intensity: Not present. Texture: Smooth. Strength: Medium.

Inflorescence:
*Type and habit*.—Cluster of cyathia surrounded by bracts.
*Quantity per lateral branch*.—1.
*Position relative to foliar plane*.—Above.
*Lastingness of inflorescence on the plant*.—4 to 5 weeks.
*Natural flowering season*.—November.
*Diameter*.—26.0 cm to 27.0 cm.
*Height*.—2.0 cm to 3.0 cm.
*Fragrance*.—Absent.

Bracts:
*Number of bracts per inflorescence*.—10 to 11.
*Shape*.—Obtuse.
*Apex*.—Acuminate.
*Base*.—Rounded.
*Margin*.—Entire.
*Size*.—Length: 8.0 cm to 13.0 cm. Width: 5.0 cm to 9.0 cm.
*Texture (both upper and lower surfaces)*.—Smooth.
*Folding along the main vein*.—Absent.
*Twisting*.—Absent.
*Rugosity between the veins*.—Weak.
*Venation pattern*.—Reticulate.
*Vein color*.—Upper surface: RHS 144B. Lower surface: RHS 145C.
*Bract color*.—Upper surface: RHS 157D. Lower surface: RHS 157D.
*Bract petiole*.—Length: 0.4 cm to 1.5 cm. Diameter: 0.2 cm. Color: Upper (part) surface: RHS 144B. Lower (part) surface: RHS 144B. Texture: Smooth Strength: Medium.

Cyme:
*Diameter*.—2.5 cm to 3.0 cm.
*Cyathia number*.—7.0 cm to 10.0 cm per inflorescence.
*Deformation of glands of the cyathium*.—Absent.
*Timing of opening of cyathia*.—Opens mid-November; first pollen appears in parallel to opening of the nectar cups, stigmas appear 2 weeks later.
*Cyathium*.—Shape: Ovate. Texture: Smooth. Diameter: 0.3 cm to 0.6 cm. Length: 0.3 cm to 0.7 cm. Color: RHS 143C.
*Peduncle*.—Color: RHS 142B. Length: 0.2 cm. Diameter: 0.1 cm. Texture: Smooth. Strength: Medium.
*Nectar cups*.—Number: 1 per cyathium. Diameter: 0.1 cm. Length: 0.3 cm to 0.4 cm. Color: RHS 10C (upper lip) and RHS 11A (lower lip). Shape: Lip shaped. Texture: Smooth.

Reproductive organs:
*Stamen quantity*.—10 to 12 per cyathium.
*Stamen shape*.—Ovate.
*Filament length*.—0.25 cm.
*Filament color*.—RHS NN155B.
*Pollen quantity*.—Sparse.
*Pollen color*.—RHS 11A.
*Gynoecium*.—Not observed.

Fruit and seed set: Not observed.

Disease and insect resistance: No particular disease or insect resistance observed.

COMPARISON WITH PARENTAL LINE AND KNOWN VARIETY

'NPCW22405' is distinguished from its mutation parent as described in Table 1:

TABLE 1

| Comparison with Parental Line | | |
|---|---|---|
| Trait or characteristic | Instant variety 'NPCW22405' | 'NPCW22279' |
| Color | White | Red |

Comparison with Similar Variety

'NPCW22405' is most similar to the commercial *Poinsettia* plant named 'Premium White' (not patented). Differences between the two varieties are described in Table 2:

TABLE 2

| Trait | Variety 'NPCW22405' | Commercial line 'Premium White' |
|---|---|---|
| Vigor | Medium | Low |
| Leaf | Wider than | Narrower than |

TABLE 2-continued

| Trait | Variety 'NPCW22405' | Commercial line 'Premium White' |
|---|---|---|
| Width | 'Premium White' | 'NPCW22405' |
| Bract | Wider than | Narrower than |
| Width | 'Premium White' | 'NPCW22405' |

I claim:

1. A new and distinct variety of *Poinsettia* plant named 'NPCW22405' as shown and described herein.

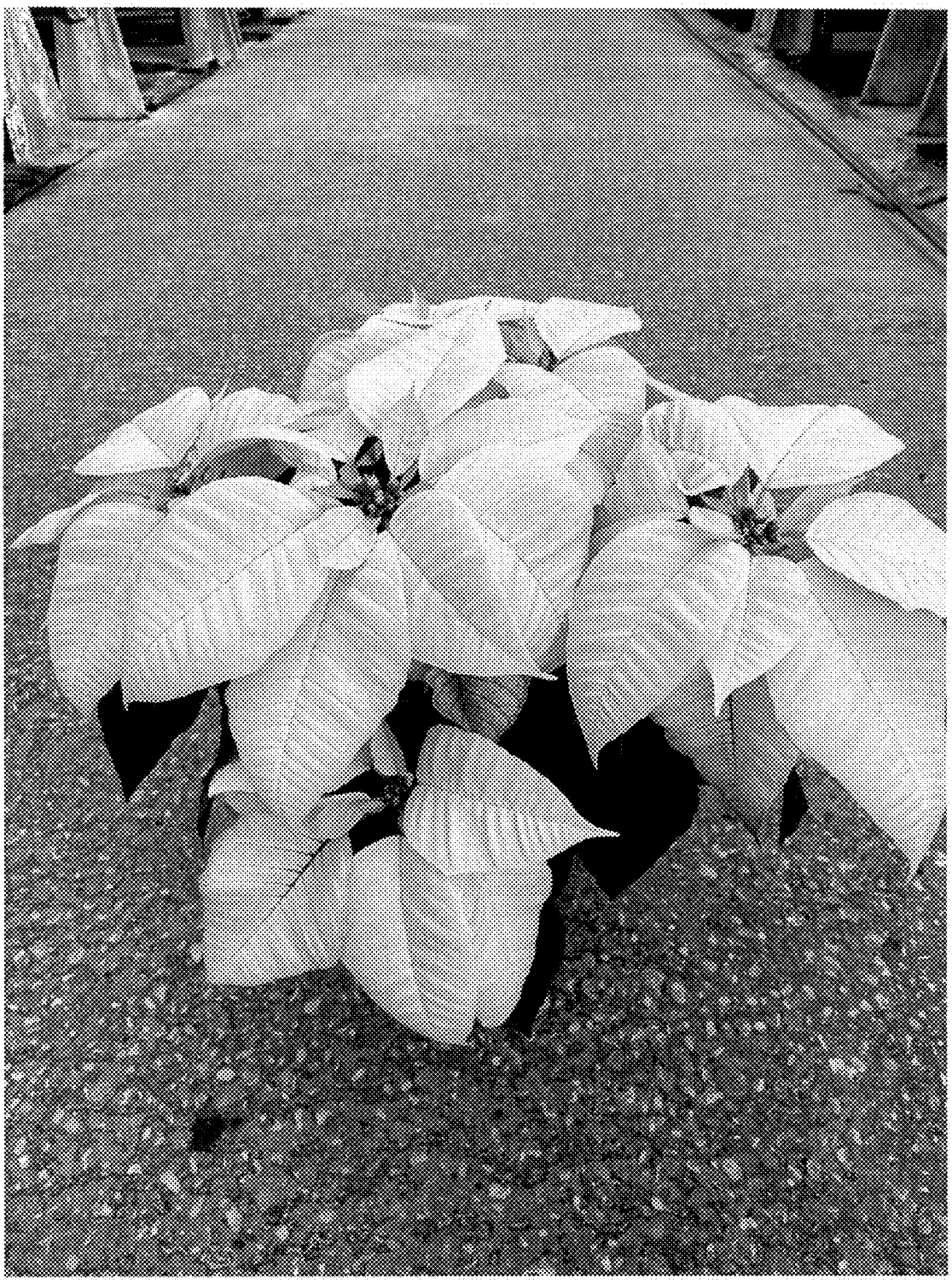

* * * * *